US009084456B1

(12) United States Patent
Zemer (10) Patent No.: US 9,084,456 B1
(45) Date of Patent: Jul. 21, 2015

(54) LINKAGE FOR JEWELRY COMPONENTS

(71) Applicant: Jack Zemer, San Diego, CA (US)

(72) Inventor: Jack Zemer, San Diego, CA (US)

( * ) Notice: Subject to any disclaimer, the term of this patent is extended or adjusted under 35 U.S.C. 154(b) by 46 days.

(21) Appl. No.: 13/887,691

(22) Filed: May 6, 2013

Related U.S. Application Data (60) Provisional application No. 61/652,289, filed on May 28, 2012.

(51) Int. Cl.
*A44C 13/00* (2006.01)
*A44C 17/00* (2006.01)

(52) U.S. Cl.
CPC .................. *A44C 13/00* (2013.01); *A44C 17/00* (2013.01)

(58) Field of Classification Search
CPC ........ A44C 5/102; A44C 5/105; A44C 5/107; A44C 11/00; A44C 11/007; B65G 17/38
USPC .............................................. 59/82, 85; 63/38
See application file for complete search history.

(56) References Cited

U.S. PATENT DOCUMENTS

| | | | | |
|---|---|---|---|---|
| 761,867 | A * | 6/1904 | Artopoens | 63/26 |
| 4,763,489 | A * | 8/1988 | Strong | 63/4 |
| 2009/0056378 | A1 * | 3/2009 | Tonali et al. | 63/38 |

* cited by examiner

*Primary Examiner* — Jack W Lavinder
(74) *Attorney, Agent, or Firm* — Gordon Rees Scully Mansukhani LLP (57) ABSTRACT

A mechanism and configuration by which one element of a jewelry piece depends from another by means of a concealed internal hook in the upper one and a loop on the lower one, with placement and orientation of said hook and loop such that the perimeters of the two elements are close when the components are connected, thus concealing said connection, and with said hooks and loops so oriented that all components tend to fall upon the long axis of the assembly, with repetition in accordance with the tastes of the user.

11 Claims, 5 Drawing Sheets

LINKAGE FOR JEWELRY COMPONENTS

CROSS-REFERENCE TO RELATED APPLICATIONS

This application claims the benefit of priority of U.S. Provisional Application No. 61/652,289, filed May 30, 2012 for Jack Zemer, which is incorporated herein by reference in its entirety.

FEDERALLY SPONSORED RESEARCH OR DEVELOPMENT

Not applicable

BACKGROUND OF THE INVENTION

1. Field

The present invention is generally in the field of jewelry, and applies specifically to jewelry comprised of multiple components linked together.

2. Jewelry

It is well understood in the jewelry industry that appearance of a product is paramount. Design features that add to appearance, beauty, interesting visual characteristics, or the perception of value are important. Anything that detracts from these attributes reduces marketability and is avoided. Jewelry designers go to great lengths to draw attention to the most important visual aspects of a product, and to minimize or conceal features that detract from the product's beauty.

Any design feature that enhances the esthetic aspects of jewelry (appearance) while concealing the necessary mechanical and practical aspects (wearability, mounting and security of gems, practicality, manufacturability, flexibility, etc.) can have a positive effect in the competitive marketplace.

Cost of production is another important factor, as complex manufacturing processes and expensive materials increase end-user price, which correlates inversely with market size or margins.

3. Coupling of Jewelry Components

Many necklaces, ear adornments, brooches, and other jewelry products are comprised of multiple elements of which one is attached to the wearer (to the ear, for example) as the primary element, and then another is connected to it by means of a formed wire eye in one and hook in another, the latter typically being manually closed during the assembly process. In some cases, the process is repeated, producing a chain of such elements, each connected to the next.

Such a process results in attractive and useful jewelry, but involves a tedious manual process that is costly due to the price of human labor. Further, the result is usually permanent and inflexible.

Another disadvantage of such loops and closed hooks is the visibility of the junctions, the mechanical form of which detracts from the appearance of the overall jewelry item.

Another disadvantage of conventional methods of attachment is that if a hook of a lower element is attached in an aperture behind the next upper element in the chain, the dependent element(s) will not ordinarily fall in a straight line below the topmost mounting point, as in an earring.

4. Prior Art

There are many known jewelry items, charm bracelets, earrings, pins, and similar products that allow the user to add and remove components, thus changing the configuration and appearance of the jewelry item. Various designs appear in patent filings and in the marketplace. In most cases, said changes are accomplished by use of clasps, screws, toggles or other moving parts, or involve costly complexity to achieve an acceptable level of security of the connection.

U.S. Pat. No. 4,245,461 by Bert, of Jan. 20, 1981, teaches jewelry comprised of links in which sheet metal loops are formed into one another, permanently. The forming of sheet metal into interconnected loops is permanent and does not enable choices by the wearer. Further, the nature of that permanent connection requires either labor to make it, or costly capital equipment to do it automatically.

U.S. Pat. No. 4,400,932 by Epstein, of Aug. 30, 1983, teaches jewelry comprised of links in which a loop of one component enters a slot in another component where it engages a flexible post, locking the two components together. This manufacturing method requires that said flexible post be deformed after engagement by said loop to make a secure connection, therefore requiring a labor step and also creating a more permanent connection that does not provide choices to the user.

U.S. Pat. No. 4,763,489 by Strong, of Aug. 16, 1988 teaches a multiple-component jewelry system with hooks and loops connecting elements thereof, where some security is achieved by using a relatively long "hook", but this design fails to provide concealment of the connecting mechanism, which detracts from the appearance of the overall result.

U.S. Pat. No. 6,446,466 by Headley, of Sep. 10, 2002, teaches a jewelry connection method in which a prong is formed into one component and a precise receptacle is formed into a second component. When the two components are to be joined, the prong is fitted into the precise receptacle at an initial angle, and moved in a prescribed fashion to a different angle at which a lock is achieved, thus accomplishing a rigid junction. While this method can be made to be invisible, and is suitable for its purpose, it is costly to execute, and lacks flexibility. Further, the tooling and fabrication required to execute each connection is complex and costly. Finally, separating the connection requires simple rotation of one component over the other in only one plane through an arc of only 115 degrees, which increases risk of unplanned separation.

U.S. Pat. No. 7,036,339 by Chiu, of May 2, 2006, teaches linked jewelry components. In some aspects of the invention, one element has a hook and another has an attachment point for said hook, and the two elements are in close proximity. This approach requires great mechanical complexity, including the bending, adhesing, or soldering of parts. Some components are of such precision as to require milling, grinding, or other metalwork after molding, also increasing production cost. Further, the hook and latch combination is so configured that it lacks the security provided by the present invention.

These and similar methods seen in patent filings and in the marketplace are often suitable for the purposes for which they were intended, but fail to achieve the goals of simplicity, cost-effectiveness of production, versatility, security of connection, ease of use, and appearance as attained by the present invention.

5. Objectives

The primary objective of the present invention is to provide a chain of some number of jewelry components that are invisibly yet securely attached one to another, thus enabling the user to assemble any number of said components into a sequence of any length, as a single piece of jewelry.

Another objective is to achieve standardized connection points of standardized geometry, permitting the joining of jewelry components that are identical or different while preserving the invisibility of the mechanical aspect of the junction.

Another objective is to create a geometry that permits all dependent elements of the jewelry system to hang in a line falling directly below the topmost center, as would be the case if the topmost center marks the center top of an earring and the jewelry elements were designed to fall directly below it with symmetry along the vertical axis of the jewelry system.

Another objective is to achieve said standardized, invisible, and simple connection points while preserving structural strength, ensuring security of the connection and reducing the probability that components will detach.

Another objective is to achieve said security while permitting the user to easily detach or add components, even when said components are of different styles, resulting in jewelry that expresses the user's taste.

Another objective is to enhance security of the connection by requiring that the two elements thereof be manipulated in at least two planes of rotation and at least 180 degrees of movement in order to separate them.

Another objective is to achieve said standardized and invisible connections in economical ways, preserving the cost-effectiveness of, and thus the market for, the end product.

BRIEF SUMMARY OF THE PRESENT INVENTION

The present invention is a connection for attaching multiple jewelry components one to another by means of a molded or soldered hook on one component and matching eye or loop on another component, creating a hidden linkage that is invisible from the frontal and side aspects, that can be repeated endlessly even when the components are combined from elements of differing jewelry, that causes all components to fall symmetrically along the vertical axis of the system, that is secure and reliable, and that is economical to manufacture.

The hook and loop comprising the connection of the present invention are configured such that they can be molded/cast, soldered/brazed/welded, or machined, and are in such a relationship that moving said loop over said hook requires that the jewelry component to which the loop is affixed travel in at least two planes of rotation, and in each of said planes through enough arc to minimize the risk of inadvertent disconnection while in use.

DETAILED DESCRIPTION OF THE PRESENT INVENTION

1. Concept

The present invention is a mechanism for jewelry that provides an easy and secure method by which the user can connect and detach modular adornments one to another. In an earring, for example, the attachment mechanism is engineered within, and concealed by, the earring itself (that portion of the item that is attached to the wearer's earlobe), and also engineered within, and concealed by, subsequent modular additions. The mechanism enables the attachment to be easily engaged and disengaged by the user, yet it provides a durable, reliable and secure fastening. This invention is not dependent upon the cosmetic design of the jewelry, but provides a specific construction and architecture of only the attachment mechanism within the jewelry.

The top of the primary component can be an earring, pendant, or brooch fastening. A user-determined number of jewelry elements can be connected to achieve any desired effect.

Because the inter-component connection is standardized in dimension, components using said standardized connections can be assembled as a sequence even if elements of said sequence are taken from various jewelry products and combined in accordance with the user's taste and design skills.

2. Construction

The invention is comprised of at least two jewelry components, a "primary" or upper one and at least one "dependent" or secondary one. The linkage between them, which represents the present invention, can be repeated as required by the design or as desired by the user.

At the bottom rear of the primary component is an aperture that is shaped as an inverted "V". In that aperture is a hook, so oriented that its shank is near-vertical and its tip is molded into an arc that continues through 180 degrees until it points down, as in the inverted letter "J" or the symbol "?". The ?-hook is molded or attached to the lowest point in the inside of the perimeter of the aperture of the primary component, and in the preferred embodiment rests within said aperture with the Y-axis of the hook (the widest part) in the same plane as the Y-axis of the primary jewelry component.

The ?-hook is so configured as to provide some dimension along the Z-axis, from the point at which it attaches to the perimeter of the aperture of the primary component until the point where it turns approximately 90 degrees to the near-vertical direction, thus providing a near-horizontal "beam" upon which a loop attached to a dependent component can rest.

At the top of the next, or dependent, component is a loop, of a size that will permit it to fit over the ?-hook and slide down its shank. The primary and dependent components are oriented so the loop passes over the tip of the ?-hook and then the dependent component is rotated with respect to the primary component so the loop passes over the curved portion of the ?-hook and down the near-vertical portion of the ?-hook, coming to rest upon the near-horizontal beam provided between the near-vertical portion of the ?-hook and the point where it is attached to the inside of the perimeter of the aperture of the primary component. To remove a dependent component requires that this manipulation be reversed in order, which is unlikely in use, therefore enhancing the security of the attachment.

The aperture in the bottom rear of the primary component is of sufficient width as to enable said loop to pass over the ?-hook without interference. In a typical embodiment, when resting upon the beam portion of the ?-hook, the loop lies in the same plane as the Y-axis of the ?-hook, enabling the primary and the dependent components to come to rest in perfect alignment, with the primary and the dependent components falling in a straight line.

If more than two components are to be assembled using this method, after the primary component each dependent component is made with a loop at the top and an aperture with a ?-hook at the bottom rear.

The key feature of the present invention is the configuration of the base of the upper component's ?-hook, which rests in an aperture that allows the loop of the lower component to slide down the shank of the hook without increasing the Z dimension (thickness) of the jewelry element.

3. Production

Figure 4:
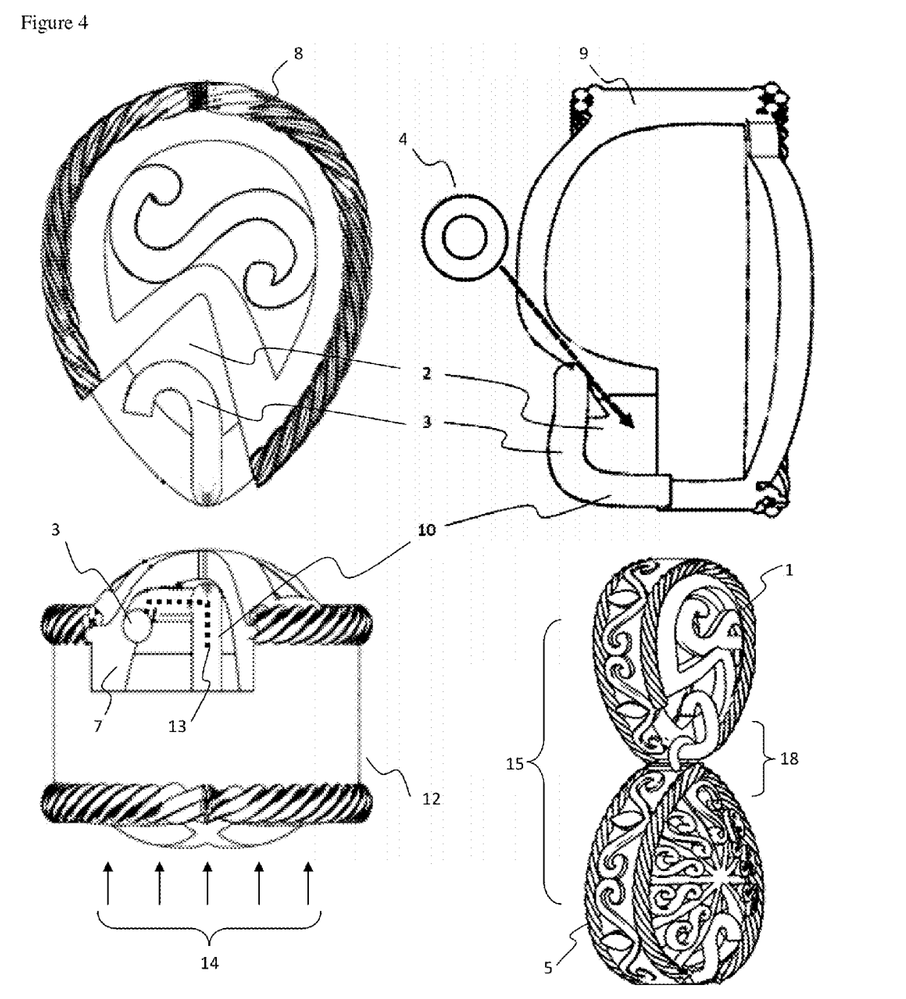
FIG. 4 shows ornate jewelry pieces incorporating the recessed hook and the loop.

The linkage of the present invention can be produced by casting (FIG. 1) or by soldering/brazing/welding the ?-hook into its required location (FIG. 4). The loop of the present invention can be produced by simple casting, with required finishing determined by the quality of the casting.

4. Advantages Over Existing Designs

Though many attempts have been made to create secure, invisible, and economical methods and mechanisms for attaching jewelry components to each other, no prior art achieves the simplicity, economy, security, and invisibility of the present invention.

5. Scope

All molded, soldered, stamped, adhesed, or otherwise constructed jewelry components that are comprised of a concealed hook in a depression or aperture in one component, and a corresponding hook in another component, so configured that when the loop is slipped over the hook and down its shank the two components are connected but the connection is hidden by the fact that the perimeters of the two components are touching, are considered within the scope of the present invention.

6. Variations

The preferred embodiment of the present invention is comprised of at least two jewelry components, of which the primary (typically upper) includes an aperture inside of which a hook is provided, and the secondary (typically lower) includes a loop that is molded or soldered, such that said loop can be oriented to feed over the tip of said hook and slid down its shank, resulting in the secondary jewelry component hanging from the bottom of the primary, with the junction itself hidden behind said components.

The concept of a hidden hook and aperture can also be executed as a flat stamped piece (tab) in one jewelry component, designed to fit within a corresponding slot in a second jewelry component when the two pieces are properly oriented as to permit such engagement, with the two pieces then returning to a hanging orientation after the flat hook and slot are engaged. This achieves goals similar to those attained by the preferred embodiment and is within the scope of the present invention, however security is compromised because engagement of said slot onto said flat tab requires manipulation through only one plane of rotation instead of two.

The concept of a hidden junction can be executed in accordance with the present invention by molding, stamping, soldering, or otherwise creating a post or other feature on the rear surface of a primary jewelry component upon which a wire loop of a secondary component can hang, such that the hanging mechanism is concealed from view.

The near-horizontal portion of the hook, upon which the loop of the next component rests, can be shaped as a letter "V", or provided with a notch, thus providing a means for precisely positioning said loop.

The configuration of hook and loop can be reversed, such that the hook is integrated into the lower jewelry component and the loop is integrated into the upper one.

The connections comprising the present invention can be so configured as to cause the jewelry components of the overall design to tilt to one side and then the other with respect to the long axis of the system, alternately or randomly, creating an attractive effect.

The present invention can be applied to a diverse product line of jewelry components in which all dimensions of the hook and loop are standardized, including standardization of the position and orientation of the hook and loop with respect to the rest of the jewelry component, enabling any combination of said components to be assembled by the user.

The present invention permits construction of secondary components with the hooks and apertures oriented in opposite directions in alternating units, thus permitting maintenance of a centerline as components are added to the chain of components, and also helping preserve the sequence intended by the designer.

Any such connection mechanism comprised of variations of such a hidden junction, concealed by the front of the jewelry, is considered to be within the scope of the present invention.

7. Description of the Drawings

Figure 1:
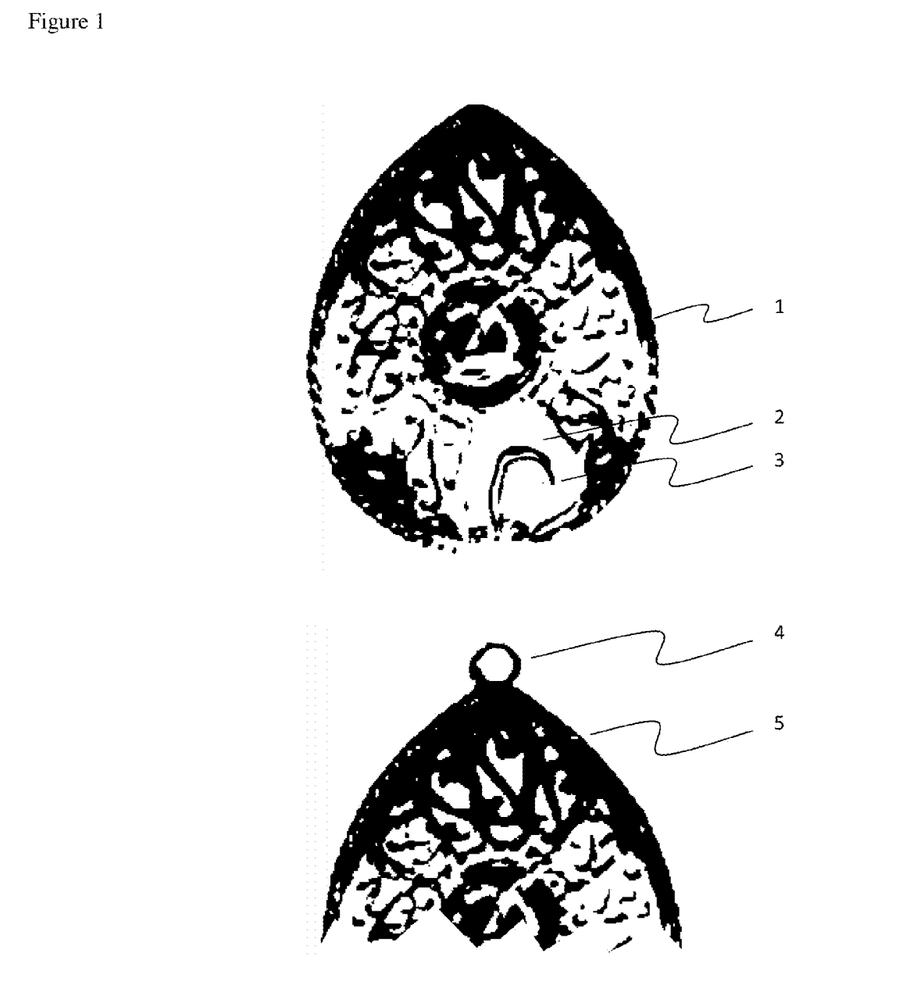
FIG. 1 shows molded/cast jewelry with two linked components.

FIG. 1 shows the initial (top) jewelry element 1 with an aperture 2 at its rear, in which a hook 3 is molded in a position to coincide with a loop 4 molded onto a secondary jewelry element 5. The positions of hook 3 and loop 4 are so configured as to ensure that the lower perimeter of element 1 and the upper perimeter of element 5 are close, thus hiding the joining method.

Figure 2:
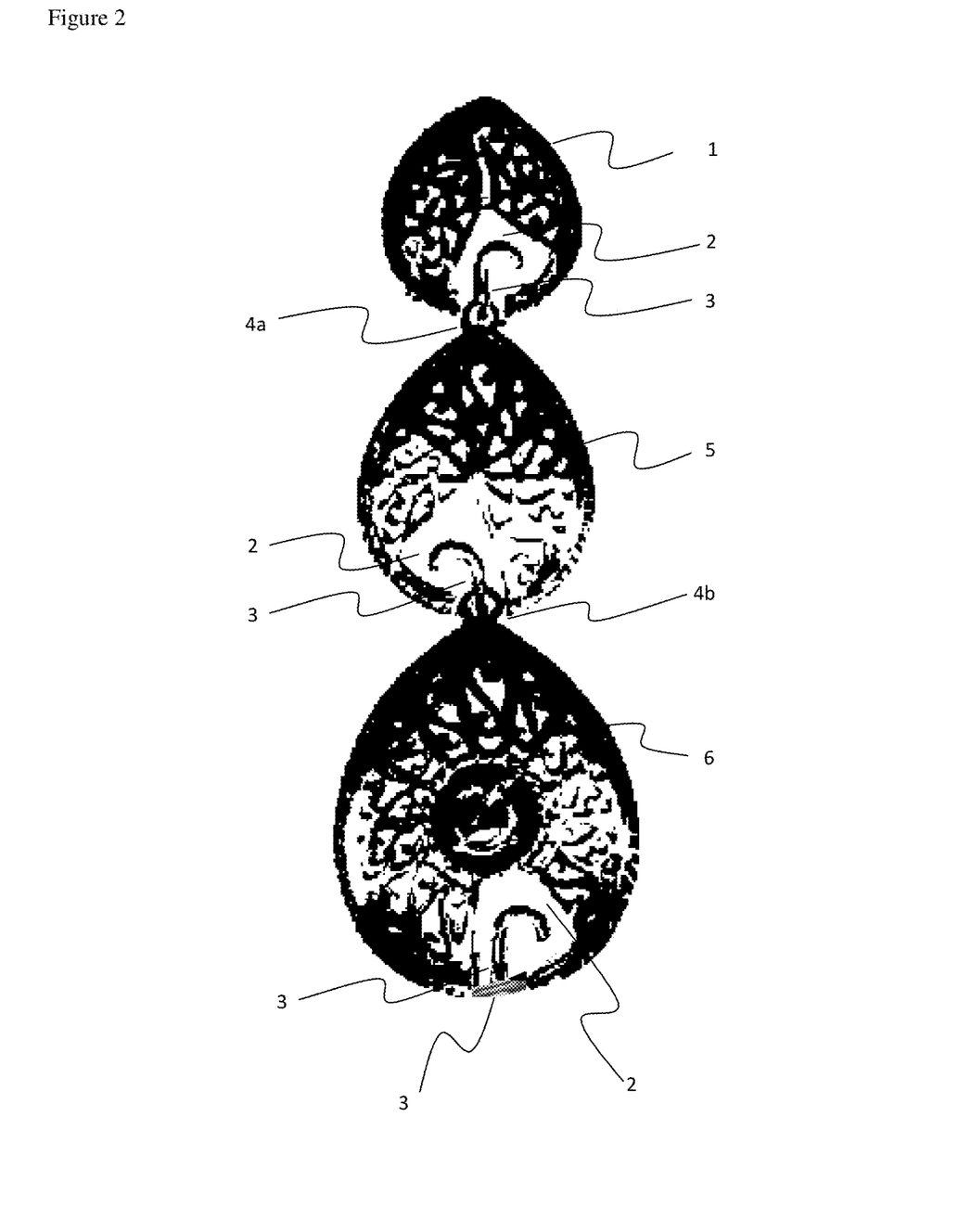
FIG. 2 shows molded/cast linked jewelry with a loop of a lower element linked to a corresponding hook at the bottom of an upper element.

FIG. 2 continues the chain of jewelry elements 1 and 5, adding a third element 6. In each element 5 and 6, the depressed (in the Z-axis) rear aperture 2 includes the inset hook 3 at the bottom to which a loop 4 is then attached.

Figure 3:
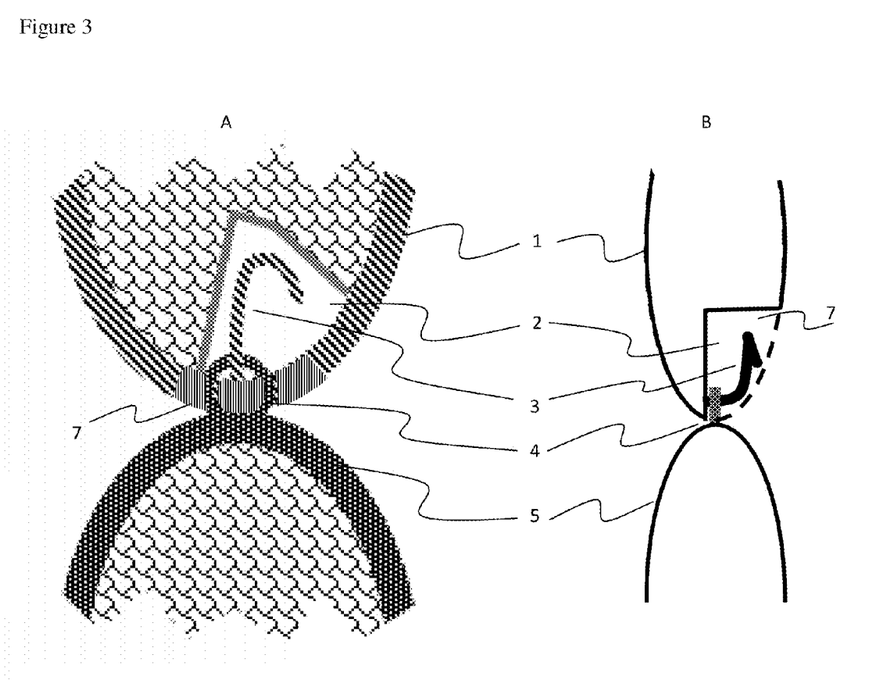
FIG. 3 shows the detail of the loop attached to the recessed hook.

FIG. 3 shows the present invention rear view A and profile B, with the same components thereof bearing the same number designators as in previous figures. However, the perimeter of the upper element 1 includes a depressed area 7 below the aperture 2, enabling the loop 4 of dependent component 5 to engage the hook 3 of upper component 1 in a manner that maintains verticality of hanging components.

FIG. 4 shows a typical primary jewelry component rear view 8 with aperture 2 containing depressed area 7 and hook 3. In side view 9, hook 3 can be seen, with the near-horizontal beam portion 10 upon which the loop of the dependent component (not shown) will hang when it moves in accordance with the arrow shown. The bottom view 12 of the jewelry component shows the hook 3 and the path (dashed line) 13 via which the loop 4 must travel to pass onto the beam 10. That bottom view 12 view also demonstrates that the depressed area 7 makes the entire coupling mechanism invisible from the frontal perspective 14 and the side perspective 9, depending on the cosmetic design of the piece. A rear view 15 that combines both a primary component 1 and dependent component 5 illustrates the resting condition of the coupling mechanism 18.

Figure 5:
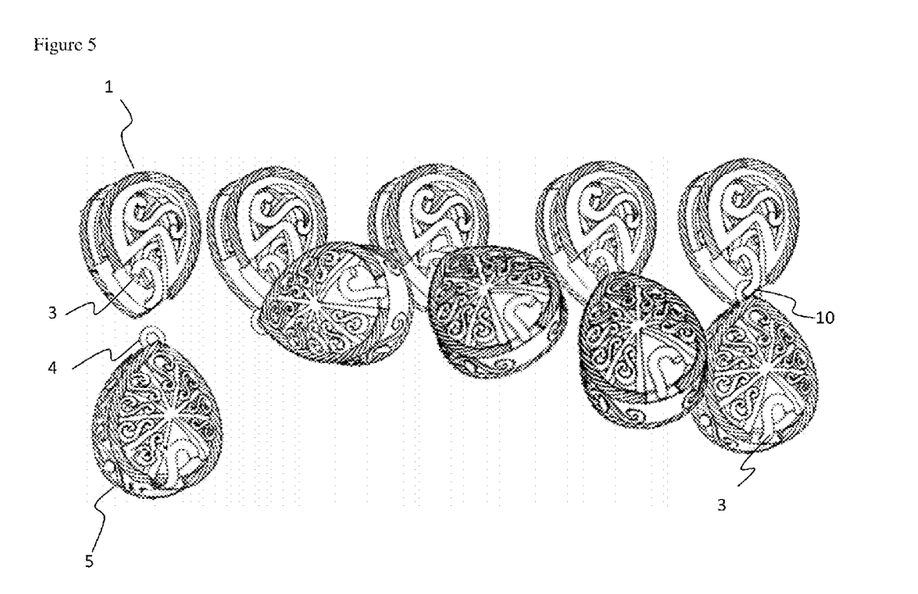
FIG. 5 shows the path taken by the loop in order to pass over the hook.

FIG. 5 demonstrates the interconnection method of the primary jewelry component 1 and dependent jewelry component 5. To make a connection, the dependent component 5 is rotated with respect to the primary jewelry component 1 until loop 4 passes over the tip of hook 3. The rotation continues until loop 4 slides along the shank of hook 3, coming to rest upon the near-horizontal beam portion 10, where gravity holds it in place, aligning the two components.

I claim:

1. A jewelry linkage system, comprising:
 a primary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  an attachment mechanism positioned in the proximal region comprising a loop or fastening; and
 a secondary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  a loop positioned in the proximal region;
 wherein the secondary jewelry component is attachable to the primary jewelry component by passing the first end of the circuitous hook through the loop and moving the loop along the path of the circuitous hook toward the second end of the circuitous hook, and wherein the hook of the primary jewelry component is not visible when the secondary jewelry component is attached to the primary jewelry component and when the first side of the primary and secondary jewelry components are viewed.

2. The jewelry linkage system of claim 1, further comprising one or more additional primary or secondary jewelry components.

3. A jewelry linkage system, comprising:
 a primary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  an attachment mechanism positioned in the proximal region comprising a loop or fastening; and
 a secondary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  a loop positioned in the proximal region;
 wherein the secondary jewelry component is attachable to the primary jewelry component by passing the first end of the circuitous hook through the loop and moving thr loop along the path of the circuitous hook toward the second end of the circuitous hook, wherein neither the hook of the primary jewelry component nor the loop of the secondary jewelry component are visible when the secondary jewelry component is attached to the primary jewelry component and the first sides of the primary and secondary jewelry components are viewed.

4. The jewelry linkage system of claim 3, further comprising one or more additional primary or secondary jewelry components.

5. A jewelry linkage system, comprising:
 a primary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  an attachment mechanism positioned in the proximal region comprising a loop or fastening; and
 a secondary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  a loop positioned in the proximal region;
 wherein the secondary jewelry component is attachable to the primary jewelry component by passing the first end of the circuitous hook through the loop and moving the loop along the path of the circuitous hook toward the second end of the circuitous hook, wherein neither the hook of the primary jewelry component nor the loop of the secondary jewelry component are visible when the secondary jewelry component is attached to the primary jewelry component and the primary and secondary jewelry components are viewed in a plane perpendicular to the first sides of the primary and secondary jewelry components.

6. A jewelry linkage system, comprising:
 a primary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  an attachment mechanism positioned in the proximal region comprising a loop or fastening; and
 a secondary jewelry component having
  a proximal region, a distal region, a first side, and a second side;
  a circuitous hook having a first end and a second end positioned on the second side in the distal region, wherein the path of the circuitous hook extends in three distinct dimensional planes between the first end and the second end;
  a loop positioned in the proximal region;
 wherein the secondary jewelry component is attachable to the primary jewelry component by passing the first end of the circuitous hook through the loop and moving the loop along the path of the circuitous hook toward the second end of the circuitous hook, wherein the secondary jewelry component is attached to the primary jewelry component, and wherein the loop of the secondary jewelry component is nested within an aperture positioned in the distal region of the primary jewelry component.

7. The jewelry linkage system of claim 6, further comprising one or more additional primary or secondary jewelry components.

8. A jewelry linkage system, comprising:
a primary jewelry component having
   a proximal region, a distal region, a first side, and a second side;
   a circuitous hook having a first end and a second end positioned on the second side in the distal region, wherein the path of the circuitous hook extends in three distinct dimensional planes between the first end and the second end;
   an attachment mechanism positioned in the proximal region comprising a loop or fastening; and
a secondary jewelry component having
   a proximal region, a distal region, a first side, and a second side;
   a circuitous hook having a first end and a second end positioned on the second side in the distal region, wherein the path of the circuitous hook extends in three distinct dimensional planes between the first end and the second end;
   a loop positioned in the proximal region;
wherein the secondary jewelry component is attachable to the primary jewelry component by passing the first end of the circuitous hook through the loop and moving the loop along the path of the circuitous hook toward the second end of the circuitous hook, wherein the distal region of the primary jewelry component and the distal region of the secondary jewelry component each comprise an aperture, and wherein the hook of each of the primary and secondary jewelry components is positioned within the aperture.

9. The jewelry linkage system of claim 8, wherein neither the hook of the primary jewelry component nor the loop of the secondary jewelry component are visible when the secondary jewelry component is attached to the primary jewelry component and the first sides of the primary and secondary jewelry components are viewed.

10. The jewelry linkage system of claim 9, wherein the loop of the secondary jewelry component is positioned within the aperture of the primary jewelry component when the secondary jewelry component is attached to the primary jewelry component.

11. The jewelry linkage system of claim 10, further comprising one or more additional primary or secondary jewelry components.

\* \* \* \* \*